United States Patent [19]

Wilber

[11] 4,407,290
[45] Oct. 4, 1983

[54] BLOOD CONSTITUENT MEASURING DEVICE AND METHOD

[75] Inventor: Scott A. Wilber, Boulder, Colo.

[73] Assignee: Biox Technology, Inc., Boulder, Colo.

[21] Appl. No.: 250,956

[22] Filed: Apr. 1, 1981

[51] Int. Cl.³ ............................................. G01N 33/16
[52] U.S. Cl. .................................... 128/633; 128/653; 128/665; 356/41; 364/416
[58] Field of Search ............... 128/632, 633, 634, 653, 128/654, 663, 665, 666, 667; 356/39, 40, 41, 42; 364/416, 417

[56] References Cited

U.S. PATENT DOCUMENTS

| 4,102,345 | 7/1978 | Cannon | 128/419 PT |
| 4,114,604 | 9/1978 | Show et al. | 356/41 |
| 4,167,331 | 9/1979 | Nielsen | 128/633 |

OTHER PUBLICATIONS

Tokatani et al. "A Solid State Noninvasive Tissue Reflectance Oximeter", Annual Conference on Engineering in Medicine and Biology, Los Angeles Hilton, 5-9, 11/77, p. 171.

Primary Examiner—Richard J. Apley
Assistant Examiner—George Yanulis
Attorney, Agent, or Firm—Daniel M. Rosen

[57] ABSTRACT

A non-invasive blood constituent measuring device and method are disclosed for measuring changes in blood thickness of predetermined blood constituents relative to total change in blood thickness at a test area to thereby determine the concentration of such constituents in the blood in a living body, which measured constituents may be, for example, hemoglobin and oxyhemoglobin to enable determination of oxygen saturation of blood. The device includes a plurality of light emitting diodes operationally controlled by timing circuitry for sequentially emitting light at different predetermined wavelengths toward a blood containing tissue sample, such as an ear lobe. A linear sensor receives emitted light passing through the sample and a train of AC modulated pulses indicative thereof is formed and then the signal representative of the light received from each emitter is scaled so that the DC components of each are normalized to a predetermined reference level with the pulse train being divided into channels at a decoder where remaining DC offset is removed and the DC component in each channel is then removed at a low pass filter, after which the AC signals in each channel are multiplexed and converted to a digital signal indicative of changes in the thickness of blood constituents for processing in a digital processor to determine therefrom the saturation of the measured blood constituents. A test unit is also included for testing operation of the device by introducing known AC modulated test signals into the circuitry.

36 Claims, 21 Drawing Figures

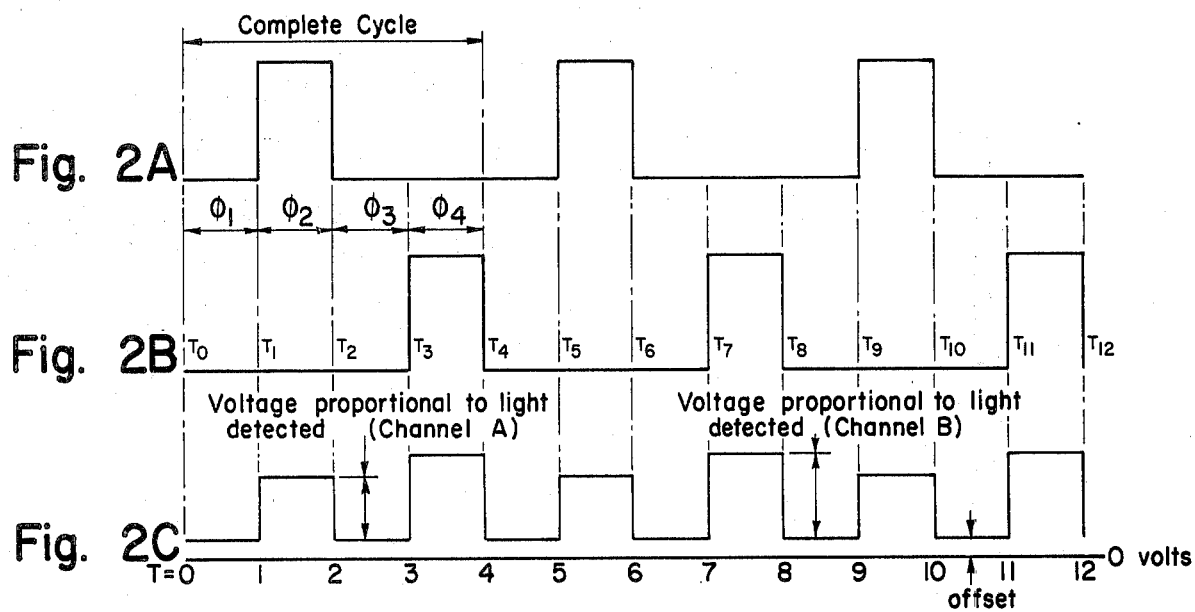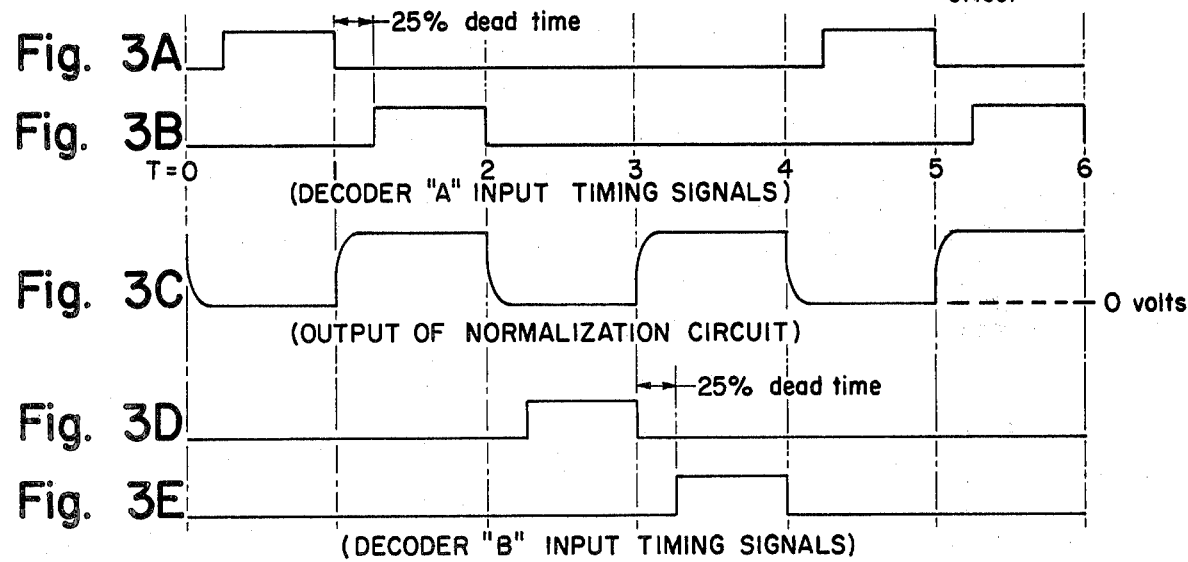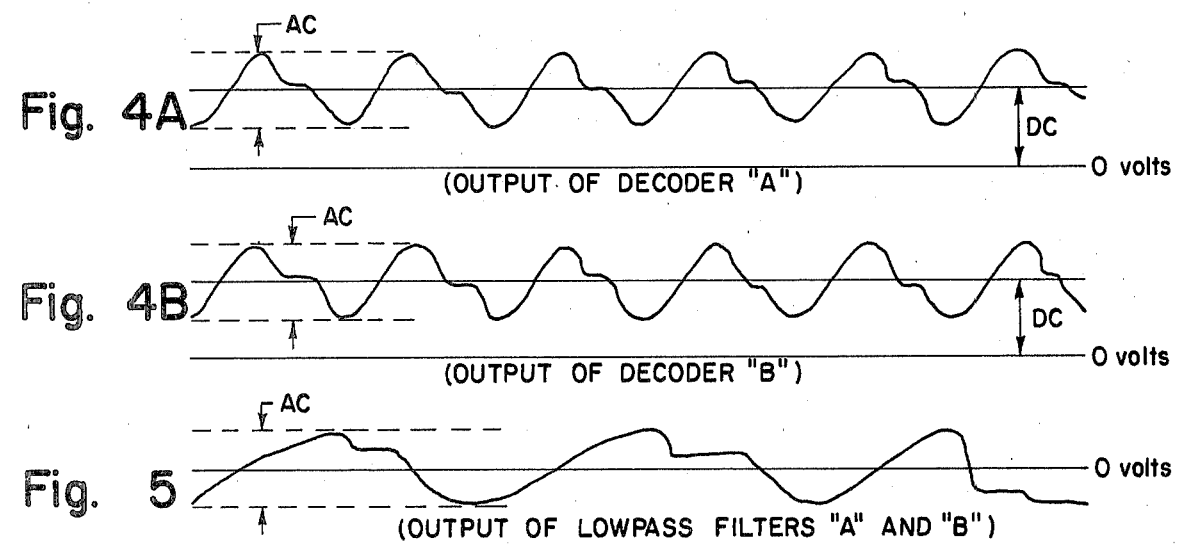

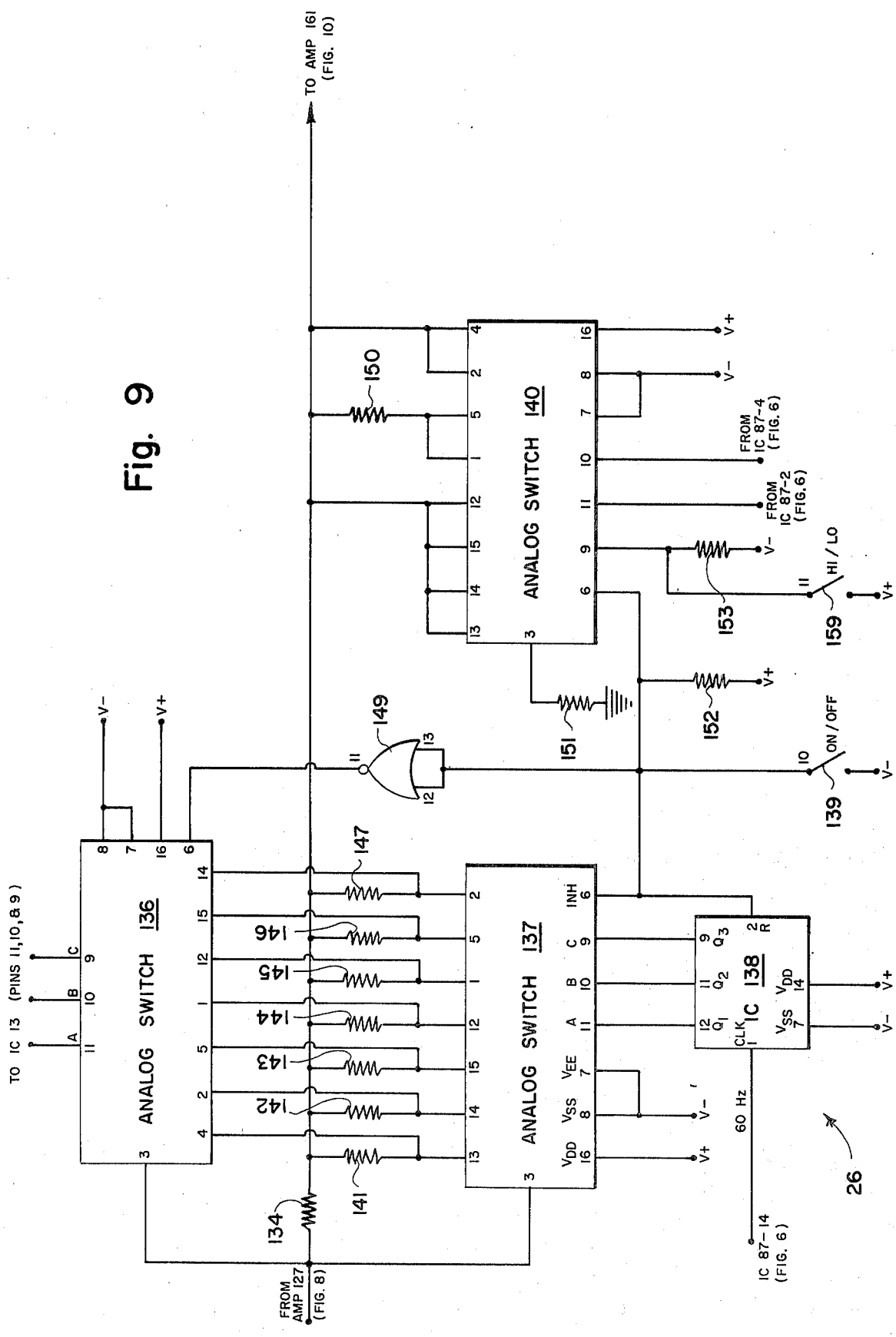

BLOOD CONSTITUENT MEASURING DEVICE AND METHOD

FIELD OF THE INVENTION

This invention relates to a blood constituent measuring device and method, and, more particularly, relates to a non-invasive device and method for determining concentration of constituents in the blood through measurement of changes in the thickness of such constituents relative to total thickness change of blood at a test area.

BACKGROUND OF THE INVENTION

As is known, one blood constituent measuring device is an oximeter which is a photoelectric photometer utilized for measurement of the fraction of hemoglobin in blood which is in the form of oxygenated Hb, which fraction is normally expressed in percentage with the percentage value being referred to as the oxygen saturation of blood. Oximetry is discussed, for example, in an article entitled "Oximetry" by Earl H. Wood, William F. Sutterer and Lucille Cronin, appearing at pages 416–445, of Medical Physics, Vol. 3, O. Glasser, Ed., Year Book Medical, Chicago, Ill. (1960).

Various oximetry devices and methods have been heretofore suggested and/or utilized, and have included devices that are non-invasive in nature as well as devices wherein the emitted light was either passed through the sample or reflected therefrom to light sensors. In addition, oximetry devices and/or methods have heretofore been suggested and/or utilized that include a plurality of light emitters operating in the red and infrared regions. Such devices and/or methods are shown, for example, in U.S. Pat. Nos. 4,167,331, 4,086,915, 3,998,550, 3,804,539, 3,704,706 (single beam), 3,647,299, and 3,638,640.

With respect to oximetry devices and methods now known, accuracy and/or dependability have often presented a problem, as has a requirement for quite complicated circuitry.

With respect to such devices and methods, it has heretofore been found necessary, for example, to use logarithmic functions in order to determine the oxygen saturation of blood (see, for example, U.S. Pat. Nos. 4,167,331, 3,998,550, 3,804,539, and 3,638,640), take derivatives of the intensity of transmitted light (see, for example, U.S. Pat. No. 4,086,915), or have used three frequencies in conjunction with three synchronous detectors, peak detectors and a ratio circuit (see, for example, U.S. Pat. No. 3,647,299) in order to determine the oxygen saturation of blood. In addition, while a digital processor has heretofore been suggested as a part of oximeter apparatus to determine oxygen saturation of blood, the oximeter apparatus also included a logarithmic amplifier (see, for example, U.S. Pat. No. 4,167,339).

While oximetry devices and/or methods have heretofore been suggested and/or utilized, none of these devices and/or methods have proved to be completely satisfactory, and improvements have therefore still been needed with respect to such devices and/or methods. In addition, a need exists for measuring devices and methods for measuring other constituents of blood such as, for example, carboxyhemoglobin, carbon dioxide in blood and/or glucose in blood.

SUMMARY OF THE INVENTION

This invention provides a blood constituent measuring device and method that is capable of measuring changes in blood thickness of predetermined constituents related to total change in blood thickness. An AC modulated pulse train is developed indicative of light received from a tissue sample at a plurality of wavelengths with the received pulses being normalized by scaling the signals developed by light from each emitter to make the average component from each light source equal, with the pulses then being separated into continuous channels and the DC component removed, and then the AC components are multiplexed and converted to digital form for processing in a digital processor.

It is therefore an object of this invention to provide a blood constituent measuring device and method.

It is another object of this invention to provide a blood constituent measuring device and method capable of determining concentrations of various constituents of blood through measurement of relative changes of the thickness of such constituents relative to total change in thickness of the blood.

It is still another object of this invention to provide a blood constituent measuring device and method that normalizes signals so that the average (DC) component from each light source is equal.

It is yet another object of this invention to provide an improved oximetry device and method that includes digital processing of received signals to determine oxygen saturation of blood.

It is still another object of this invention to provide a blood constituent measuring device and method that includes providing an AC modulated test signal for testing of the device.

With these and other objects in view, which will become apparent to one skilled in the art as the description proceeds, this invention resides in the novel construction, combination, arrangement of parts and method substantially as hereinafter described and more particularly defined by the appended claims, it being understood that such changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which:

FIGS. 2A, 2B and 2C show timing diagrams for the LED drivers and current to voltage converter shown in FIG. 1;

FIGS. 3A, 3B, 3C, 3D and 3E show input timing diagrams for the decoder shown in FIG. 1;

FIGS. 4A and 4B depict typical outputs for the decoder shown in FIG. 1;

FIG. 5 depicts a typical output for the low pass filters shown in FIG. 1;

FIG. 9 is a block and electrical schematic of the test unit utilized in this invention;

DESCRIPTION OF THE INVENTION

Figure 1:
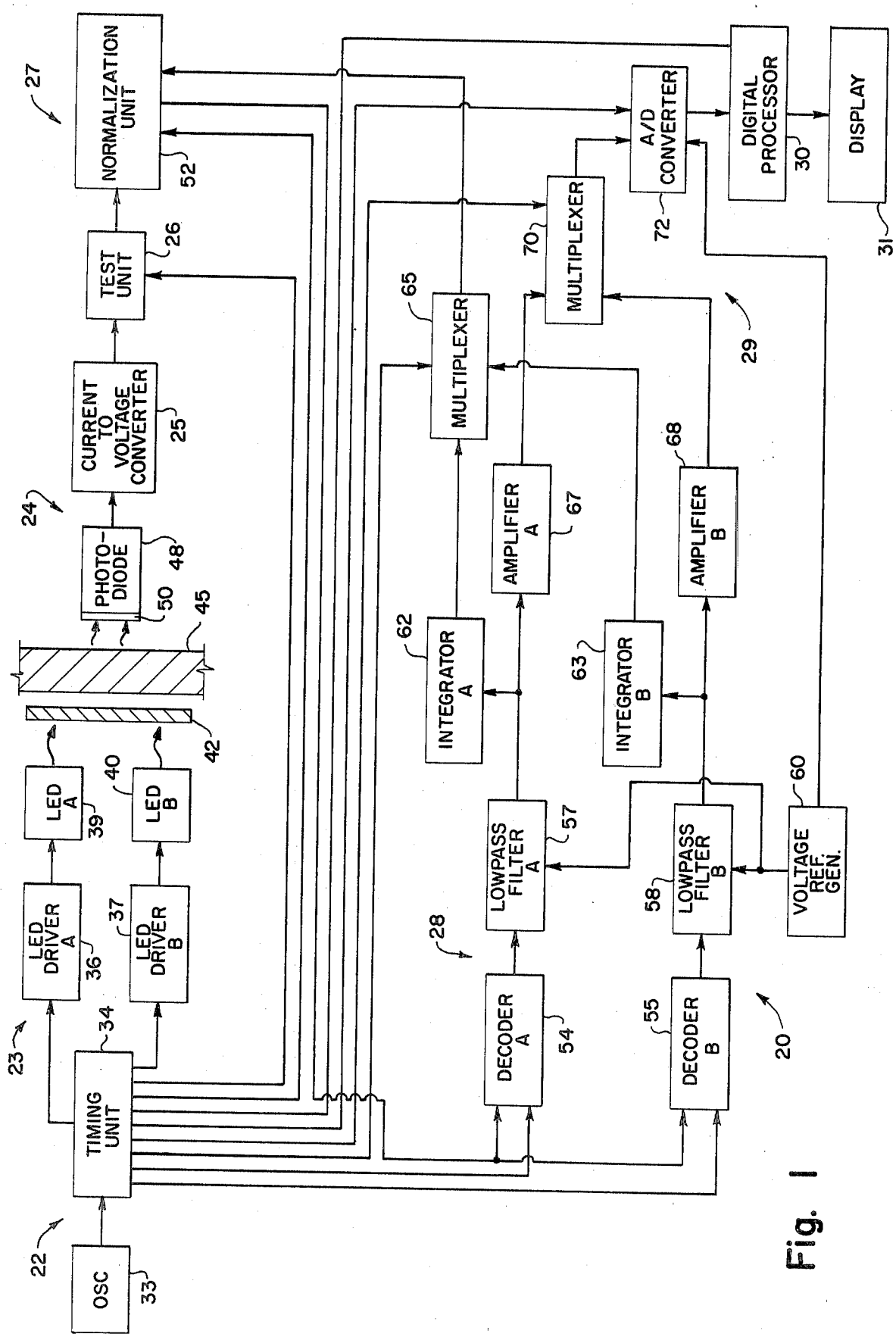
FIG. 1 is a block and schematic diagram of the oximeter of this invention.

Referring now to the drawings, the device 20 of this invention is shown in block and schematic form as an oximeter, by way of example, to determine oxygen saturation of blood. The device includes a signal generating and timing section 22, a light emitting section 23, a light sensing section 24, a signal converting section 25, a device testing section 26, a normalizing section 27, a demultiplexing section 28, a multiplexing and signal conversion section 29, a digital processing section 30 and a display section 31.

Signal generating and timing section 22 provides timing signals for the device and includes an oscillator 33 connected with a timing circuit 34 which supplies a plurality of outputs at different related frequencies, as is conventional.

As indicated in FIG. 1, timing unit 34 provides output signals to LED drivers 36 and 37, which drivers are connected with light emitting diodes (LEDs) 39 and 40, respectively, to cause selective and sequential energization of each LED. As shown in the timing diagrams of FIGS. 2A and 2B, each LED is preferably energized for 25% of each energization cycle of LED's 39 and 40 (i.e., LED 39 is energized during the time period from T1 to T2 with the time period T0 to T1 providing a zero reference for channel A, and LED 40 is energized during the time period T3 to T4 with the time period T2 to T3 providing a zero reference for channel B).

LED's 39 and 40 emit light at different frequencies with LED 39 preferably emitting light in the red region and LED 40 preferably emitting light in the infrared region. LEDs 39 and 40 could, however, emit light in different regions as desired so long as the absorption characteristics differ when passing through the blood-containing tissue, this being essential to determining the value of oxygen saturation in the blood as is well known. In addition, while the light emitters are indicated herein to be light emitting diodes, it is to be realized that other sources of electromagnetic energy might be utilized, and it is likewise to be realized that the electromagnetic source could include a plurality of wavelengths and the sensors could be responsive to selected wavelengths.

As indicated in FIG. 1, device 20 of this invention is a non-invasive device, with the light emitted from LEDs 39 and 40 being preferably directed through a light diffusing disc 42 to the blood containing sample 45 to be tested, which sample may be, for example, tissue such as an ear lobe or the like. At the opposite side of sample 45, light passing through the tissue is sensed at light sensing section 24, which includes a linear sensing device, which may be a photodiode 48 (or an array of such diodes).

An electronic shield 50 in preferably positioned in the light path over the front of the photodiode and such a shield may be as described and claimed in a U.S. patent application entitled "Improved Photodetector" by Scott A. Wilber.

The current developed at light sensing element 48 is coupled to current to voltage convertor 25, where a train of pulses (as shown in FIG. 2C) is developed (due to the duty cycle of emitted light from the LEDs) with the height of the pulses being dependent upon the amount of light passing through the tissue and the amount of DC offset introduced due to factors such as ambient light. In addition, the pulses are AC modulated (not shown in FIG. 2C) due to blood pulsations in the tissue sample then at the test area.

The pulse train output from converter 25 is coupled through test unit 26 to normalization unit 52 of normalizing section 27 where the signal representative of the light received from each emitter is scaled so that the DC components of each are normalized to a predetermined reference level and the DC voltage offset due to ambient light and the like is also removed from the pulses (through charging of capacitors in the normalization unit to a voltage equal to the offset as brought out more fully hereinafter) to produce an output pulse train signal as shown in FIG. 3C. The normalization circuit functions to scale both the AC and DC components of each signal so that the DC (average) component is made equal to a known, preset level. The mathematical transformation is:

$$AC_{(output)} = K \left[ \frac{AC_{(input)}}{DC_{(input)}} \right], \; DC_{(output)} = K$$

where K=1.5 (specific to embodiment shown). It is to be understood that the normalization is performed on the peak to peak amplitude of the pulses.

The pulse train output signal from normalization unit 52 is coupled to demultiplexing section 28, and, more particularly, is coupled to decoders 54 and 55 therein. Decoders 54 and 55 (which function as sample and hold circuits) also receive timing signals from timing unit 34 (as shown in FIGS. 3A and B and 3D and E) to provide a 25% dead time at the beginning of each pulse received from normalization unit 52 to allow the photodiode and other circuitry to settle within their limited rise and fall times.

Typical outputs from decoders 54 and 55 are shown in FIGS. 4A and 4B as an AC component riding on a DC component (the relative size of the AC component is highly exagerated). This output is coupled to low pass filters 57 and 58 which filters also receive an input from voltage reference generator 60. As shown in FIG. 5, the low pass filters also operate to subtract the DC voltage supplied by generator 60 from the input signal to produce an output signal that is essentially an AC component on a zero reference level.

The outputs of channels A and B (i.e., the outputs from filters 57 and 58) are coupled to integrators A and B (designated in FIG. 1 as integrators 62 and 63), respectively. The outputs from integrators 62 and 63 are coupled to multiplexer 65 with the output from multiplexer 65 being coupled to normalization unit 52 to supply the signals needed to adjust the amplitudes of signals A and B so that their DC components are precisely equal.

The outputs from channels A and B are also coupled through amplifiers 67 and 68 to multiplexer 70 of multiplexing and signal converting section 29. Multiplexer 70 samples both inputs simultaneously at a rate of 30 times per second and holds the two levels until analog to digital (A/D) convertor 72 has converted each incoming analog signal to a digital signal and has transferred the data to digital processor 30 (which data conversion and transfer occurs before the next sample needs to be taken, i.e., within 1/30th of a second). While multiplexing and demultiplexing of signals are indicated herein, it is to be realized that other techniques as would be obvious to one skilled in the art could also be utilized. In addition, the analog signals could be digitized at any point after being developed in current to voltage converter 25 and then processed by a digital processor appropriately programmed.

Figure 6:
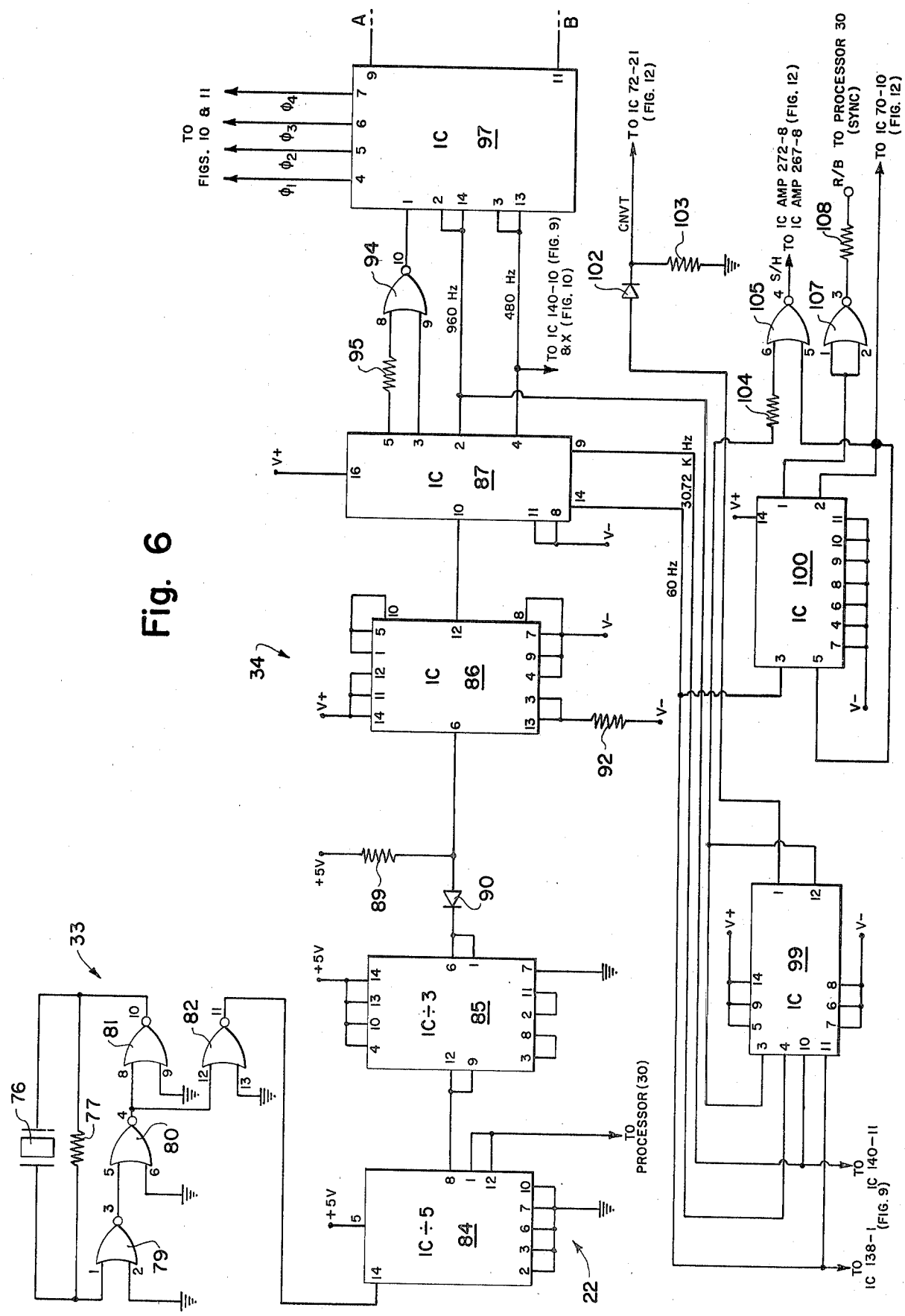
FIG. 6 is a block and electrical schematic of the oscillator and timing unit utilized in this invention.

Digital processor 30 is preferably comprised of a 6502 Digital Micro-Processor and associated RAM and ROM, and is connected with A/D converter 72 through tristate buffers and a data bus, as is conventional. As shown in FIG. 6, processor 30 also preferably receives timing and sync inputs from timing units 34. The output of digital processor 30 is preferably displayed at display 31 in conventional manner. Display 31 can be a visual display and/or can include a hard copy readout such as, for example, a strip chart recorder.

Figure 8:
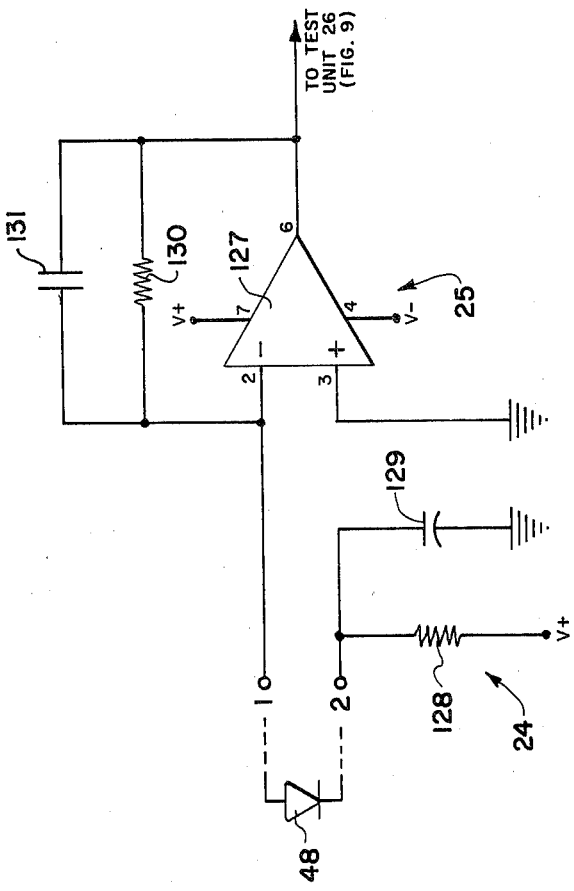
FIG. 8 is a block and electrical schematic of the photodiode and current to voltage converter utilized in this invention.
Figure 7:
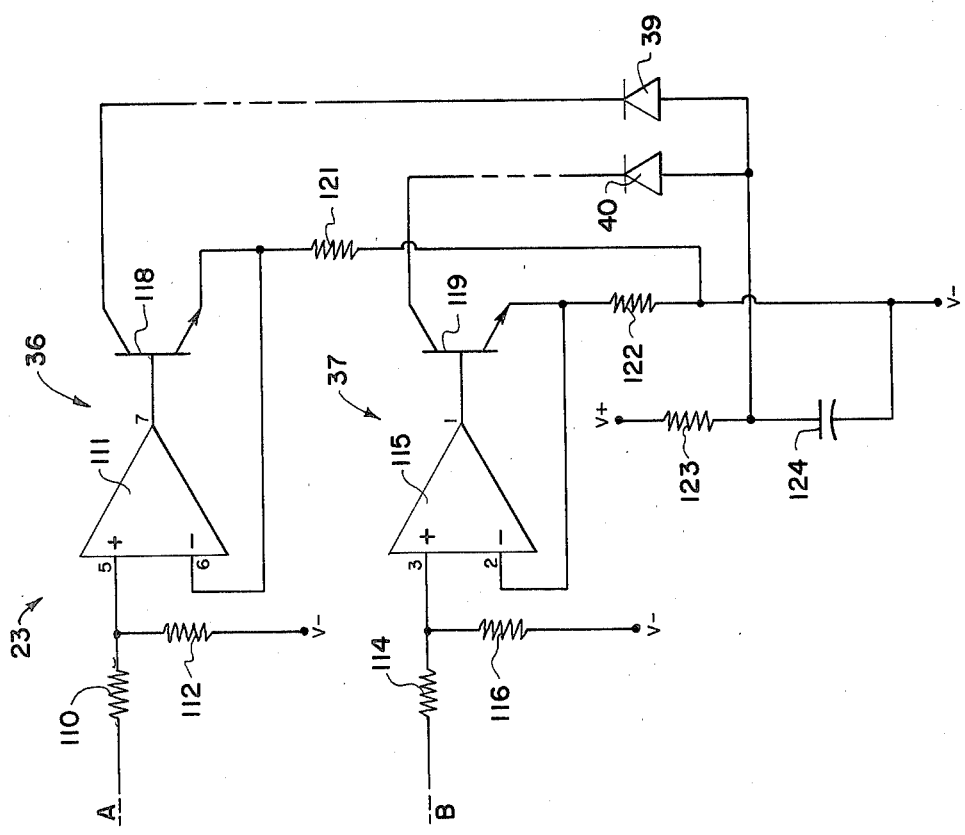
FIG. 7 is a block and electrical schematic of the LED drivers and LEDs utilized in this invention.
Figure 10:
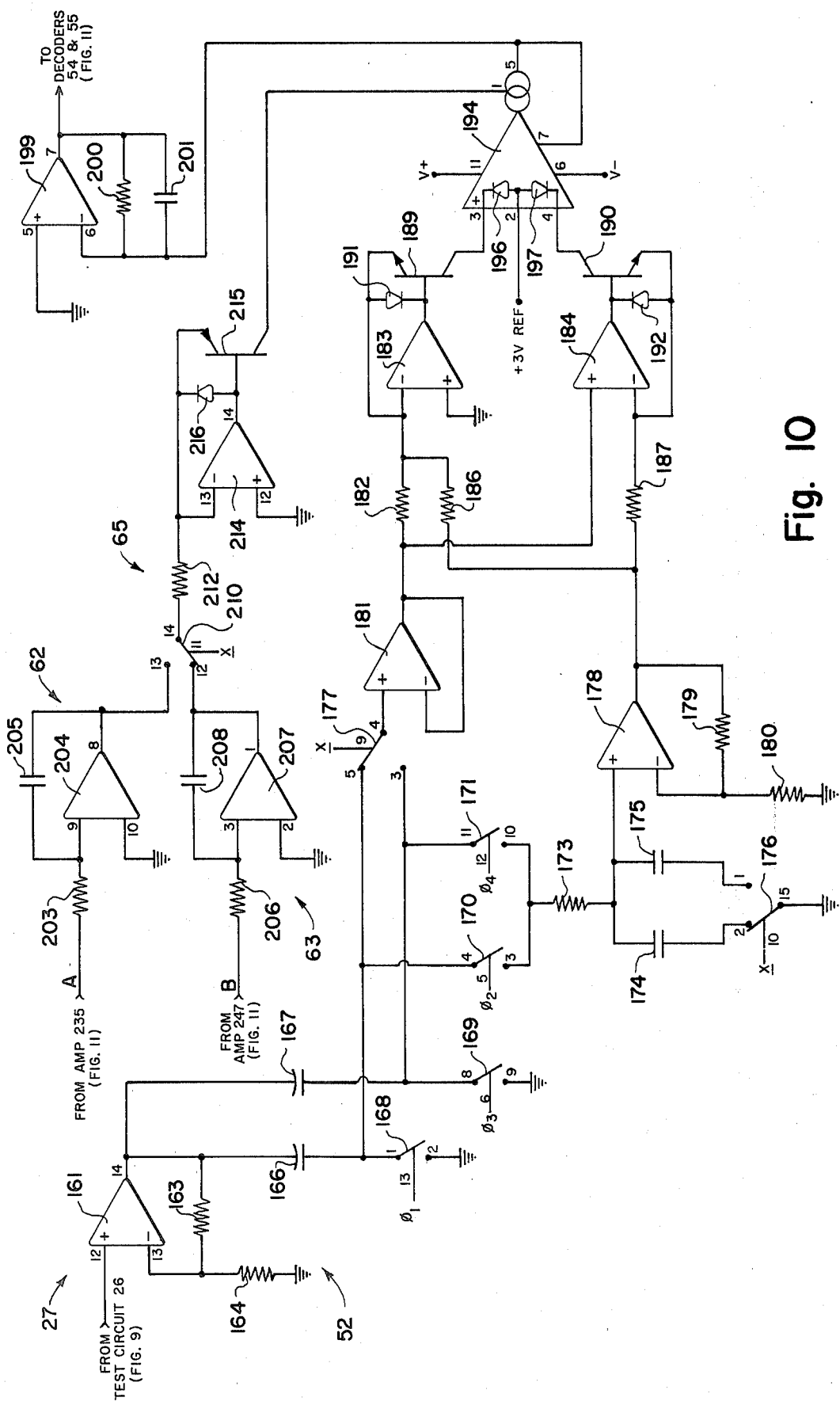
FIG. 10 is a block and electrical schematic of the normalization section utilized in this invention and including the integrators 62 and 63 and multiplexor 65 of FIG. 1.
Figure 11:
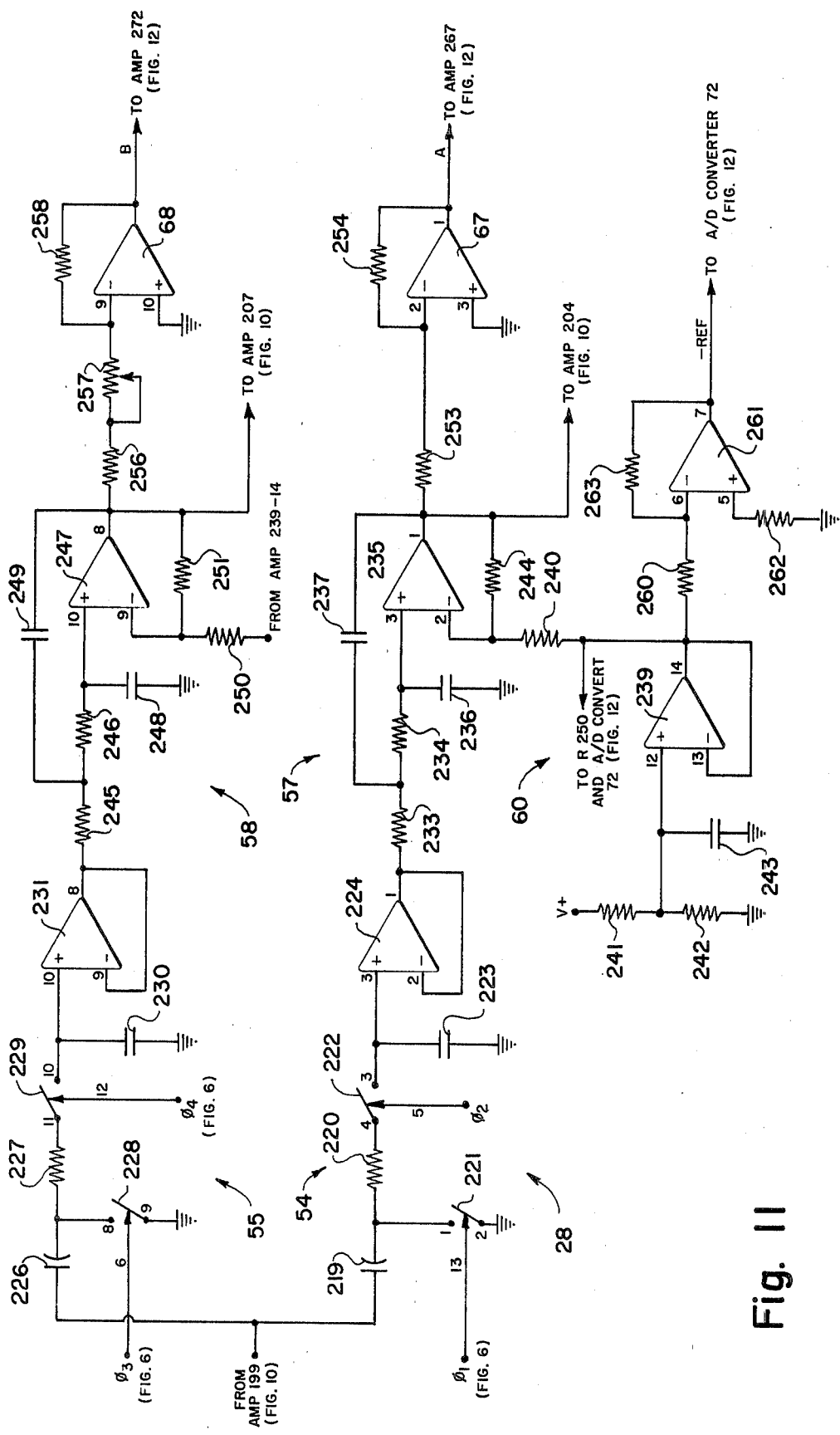
FIG. 11 is a block and electrical schematic of the decoders, low pass filters and amplifiers utilized in this invention.
Figure 12:
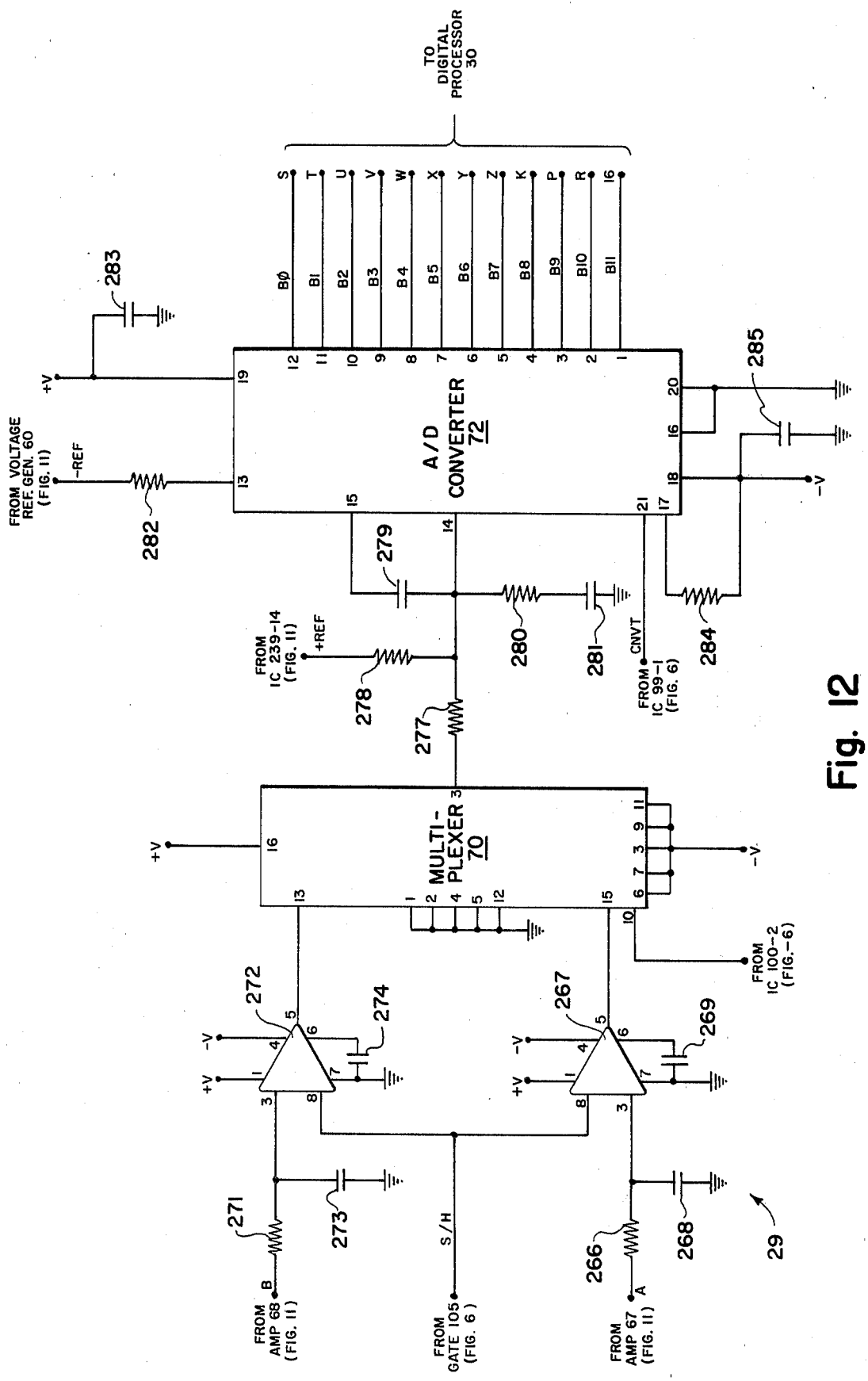
FIG. 12 is a block and electrical schematic of the multiplexer and A/D converter utilized in this invention.
Figure 13:
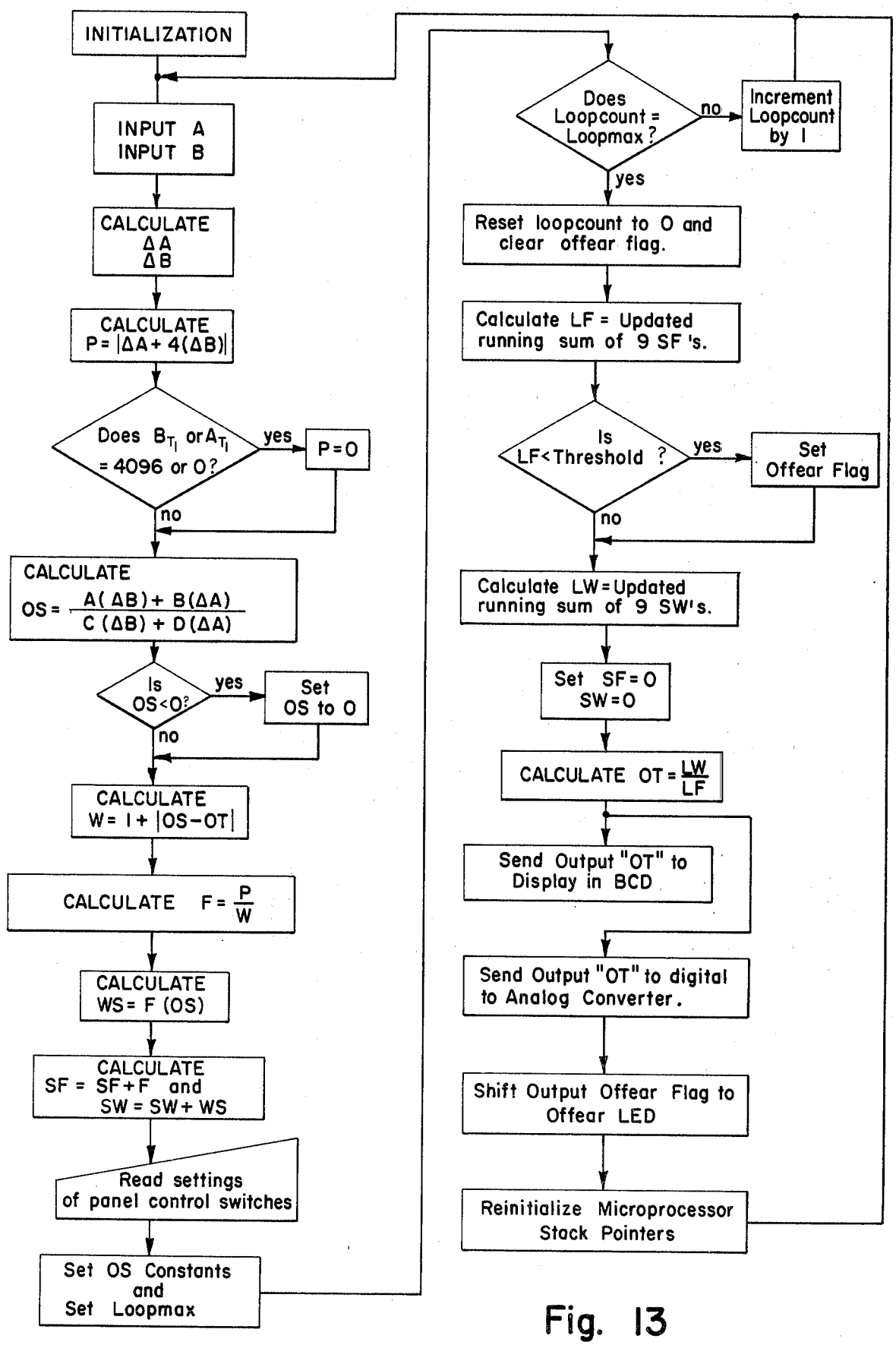
FIG. 13 is a processor flow diagram for the digital processor utilized in this invention.
Figure 14:
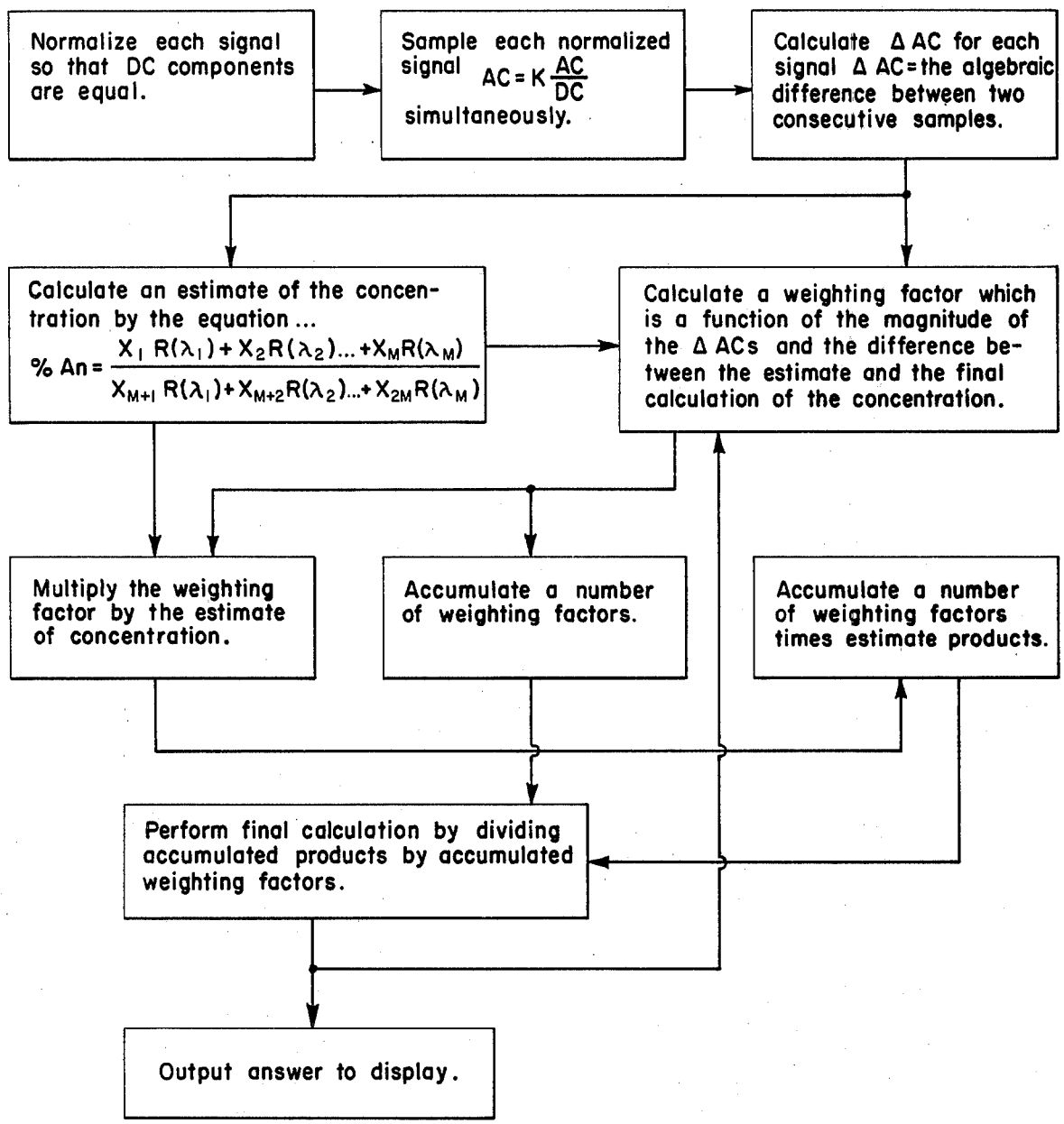
FIG. 14 is a general algorithm for processing in the digital processor as shown by the flow diagram of FIG. 13.

Referring to FIGS. 6 through 12, a more detailed schematic and block diagram with respect to this invention is shown with the signal generating and timing section being shown in FIG. 6, light emitting section 23 being shown in FIG. 7, light sensing section 24 and signal converting section 25 being shown in FIG. 8, device testing section 26 being shown in FIG. 9, normalizing section 27 and related integrators 62 and 63, and multiplexer section 65 being shown in FIG. 10, demultiplexing section 28 being shown in FIG. 11, multiplexing and signal conversion section 29 being shown in FIG. 12, and a flow diagram and operating algorithm for processor 30 being shown in FIGS. 13 and 14.

As shown in FIG. 6, oscillator 33 includes a 1.832 MHz crystal 76 having a resistor 77 connected in parallel therewith. NOR gate 79 has one input connected to one side of crystal 76 and the output connected as one input to NOR gate 80. The output of NOR gate 80 is connected as one input to NOR gates 81 and 82 with the output of NOR gate 81 being connected to the other side of crystal 76 and the output of NOR gate 82 providing the oscillator output to timing circuitry 34. The remaining input of gates 79, 80, 81 and 82 are connected with ground.

The output of oscillator 33 is coupled to a countdown chain consisting of series connected integrated circuits 84, 85, 86 and 87, with integrating circuit 84 providing a timing signal output to processor 30. As shown in FIG. 6 (and throughout FIGS. 6 through 12), various connections between components, to positive and negative voltage sources, and to ground, are shown either as direct connections or through components such as resistors, capacitors and/or diodes which have been numbered and illustrative values for the same can be found in the table of components hereinafter set forth.

As shown in FIG. 6, pin 5 of integrated circuit 87 is connected with one input of NOR gate 94 through resistor 95, while the other input is connected with pin 3 of integrated circuit 87, and the output of NOR gate 94 is connected to pin 1 of integrated circuit 97. In addition, a 960 Hz input and a 480 Hz input is provided to integrated circuit 97 from integrated circuit 87, with the 480 Hz output from integrated circuit 87 also being coupled to test unit 26 (FIG. 9) and to normalization circuit 52 (FIG. 10) and with the 960 Hz signal also being coupled to test unit 26 (FIG. 9).

Timing signal outputs (at 240 Hz) are coupled from integrated circuit 97 on pins 9 and 11 to LED drivers 36 and 37 for channels A and B, respectively. In addition, timing outputs designated as ∅1, ∅2, ∅3 and ∅4 are provided on pins 4, 5, 6 and 7, respectively, to provide switching at normalization unit 52 (FIG. 10).

The 30.72 KHz output from integrated circuit 87 is coupled to pin 4 of integrated circuit 99, while the 60 Hz output from integrated circuit 87 is coupled to pin 11 of integrated circuit 99 and to pin 3 of integrated circuit 100 with a 60 Hz output also being coupled to test unit 26 (FIG. 9).

The output of pin 1 of integrated circuit 99 is coupled through diode 102 (having resistor 103 to ground connected thereto) to provide a CNVT output to A/D convertor 72 (FIG. 12), while pins 3 and 12 are connected through resistor 104 as one input to NOR gate 105 (the other input of gate 105 is connected to pins 2 and 5 of integrated circuit 100), which gate provides the S/H output to multiplexer unit 70 (FIG. 12).

The output on pin 1 of integrated circuit 100 is coupled through NOR gate 107 and resistor 108 to provide a R/B output to processor 30 (as a sync input signal to the processor), while pins 2 and 5 are connected to the multiplexer unit 70 (FIG. 12).

Referring now to FIG. 7, the channel A input from integrated circuit 97 is coupled through resistor 110 to the positive input of amplifier 111 of LED driver 36, while the channel B input from integrated circuit 97, is coupled through resistor 114 to the positive input of amplifier 115 of LED driver 37.

The output of amplifier 111 is connected to the base of transistor 118 the emitter of which is connected to the negative input of amplifier 111. In like manner, the output of amplifier 115 is connected to the base of transistor 119 the emitter of which is connected to the negative input of amplifier 115. The collector of transistor 118 is connected with one side of LED 39, while the collector of transistor 119 is connected with one side of LED 40, with the other side of the LEDs being connected to the positive voltage power source through resistor 123.

Referring now to FIG. 8, one side of photodiode 48 is shown connected to the negative input of amplifier 127, while the other side of the photodiode is connected with the power source through resistor 128 (and with ground through capacitor 129). The output from amplifier 127 is coupled to test unit 26 (FIG. 9).

Referring now to FIG. 9, the output from amplifier 127 of current to voltage convertor 25 is coupled through resistor 134 of test unit 26 to the output of the unit (so that the signals are coupled through the unit when the test unit is off) and to pin 3 of analog switches 136 and 137. Timing signals for switches 136 and 137 are provided by integrated circuit 138 which receives a 60 Hz clock input from timing unit 34 and, more particularly, from integrated circuit 87 pin 14 (FIG. 6).

Test unit 26 is utilized only for test purposes and is not in circuit during operation of the device to determine the oxygen saturation of a tissue sample, the unit being switched off and on by off/on switch 139.

Oximeter device 20 is tested by use of test unit 26. During test, there is no incoming signal, i.e., there is no tissue sample then being tested. Instead, test unit 26 supplies a test signal to both channels A and B through use of analog switches 136, 137 and 140 and resistors 141 through 147 to switch the modulation envelope and supply modulation of a known percentage of amplitude to channels A and B. In addition, a high-low switch 159 is provided to pin 9 of analog switch 140.

Referring now to FIG. 10, the output from test circuit 26 (or the signal coupled through resistor 134 from current to voltage convertor 25) is coupled to the positive input of amplifier 161 of normalization unit 52. Amplifier 161 has a gain of two and has a high impedance input. The output from amplifier 161 is connected with one side of parallel connected capacitors 166 and 167, the other sides of which are connected with ground through switches 168 and 169, respectively, and are connected through switches 170 and 171, respectively, to a low pass filter.

Switches 168 and 169, and 170 and 171, are controlled by timing outputs from pins 4, 6, 5 and 7, respectively, of integrated circuit 97 (FIG. 6). The low pass filter connected to switches 170 and 171 includes resistor 173 connected to one side of capacitors 174 and 175, the other side of which are connected with ground through switch 176. Switch 176 (along with switch 177 which is also connected with capacitors 166 and 167) is controlled by the 480 Hz output from integrated circuit 87 (FIG. 6). The junction of resistor 173 and capacitors 174 and 175 is also connected with the positive input of amplifier 178 which functions as an impedance converter with a low impedance output.

Amplifier 181, connected with switch 177, also functions as a voltage to current converter and provides a low impedance output through resistor 182 to the negative input of amplifier 183 and to the positive input of amplifier 184. Amplifiers 183 and 184 provide outputs to the bases of transistors 189 and 190 to form, in association therewith, voltage to current converters with the outputs from the collectors of transistors 189 and 190 being coupled to the positive and negative inputs, respectively, of operational transconductance amplifier 194. Amplifier 194 includes linearizing diodes 196 and 197 and the output is a current source output that is coupled through buffer amplifier 199 to provide an output to decoders 54 and 55 (FIG. 11).

Normalization circuit 52 also receives an input at operational tranconductance amplifier 194 from multiplexer 65 of the normalizing section which, in turn, receives inputs from integrators 62 and 63 connected with channels A and B, respectively. The input from channel A is coupled through resistor 203 to amplifier 204 of integrator 62, while the input of channel B is coupled through resistor 206 to amplifier 207 of integrator 63.

The outputs from the integrators are coupled to switch 210, which switch is controlled by the 450 Hz timing signal from integrated circuit 87 (FIG. 6) for control of this switch in the same manner as switches 176 and 177 are controlled. The movable contact of switch 210 is connected through resistor 212 and a voltage to current converter consisting of amplifier 214, transistor 215 and diode 216, which converter provides a low impedance output to the output side of operational transconductance amplifier 194.

Referring now to FIG. 11, the output from normalization circuit 52 is coupled from amplifier 199 to decoders 54 and 55 (defining channels A and B, respectively). The input to decoder 54 is coupled through capacitor 219 (for offset removal) to resistor 220, the junction of which has a switch 221 to ground, and then through switch 222 to capacitor 223 (to ground) and to the positive input of amplifier 224 (to form a sample and hold circuit). Switches 221 and 222 are controlled by the $\emptyset 1$ and $\emptyset 2$ inputs from integrated circuit 97 (FIG. 6), and amplifier 224 functions as an impedance converter with a low impedance output.

In like manner, the input to decoder 55 is coupled through capacitor 226 (for offset removal) to resistor 227, the junction of which has a switch 228 to ground, and then through switch 229 to capacitor 230 (to ground) and to the positive input of amplifier 231 (to form a sample and hold circuit). Switches 228 and 229 are controlled by the $\emptyset 3$ and $\emptyset 4$ inputs from integrated circuit 97 (FIG. 6), and amplifier 231 functions as an impedance converter with a low impedance output.

The output from decoder 54 is coupled through resistors 233 and 234 to the positive input of amplifier 235 of low pass filter 57. The positive input of amplifier 235 has a capacitor 236 to ground connected thereto, and the output is connected with the junction of resistors 233 and 234 through capacitor 237. Filter 57 is an active filter with a gain of 2, and receives an input from voltage reference generator 60, and, more particularly, from the output of amplifier 239 of generator 60, at the negative input of amplifier 235 through resistor 240.

In like manner, the output from decoder 55 is coupled through resistors 245 and 246 to the positive input of amplifier 247 of low pass filter 58. The positive input of amplifier 247 has a capacitor 248 to ground connected thereto, and the output is connected with the junction of resistors 245 and 246 through capacitor 249. Filter 58 is an active filter with a gain of 2, and receives an input from voltage reference generator 60, and, more particularly, from the output of amplifier 239 of generator 60, at the negative input of amplifier 247 through resistor 250.

Voltage reference generator 60 is used to provide a voltage to the low pass filters to subtract the DC component from the incoming signal in each channel.

The output from low pass filter 57 is coupled from the output of amplifier 235 to amplifier 204 of integrator 62 (FIG. 10) and through resistor 253 to the negative input of amplifier 67, the output of which is coupled to multiplexer 70 (FIG. 12). In like manner, the output from low pass filter 58 is coupled from the output of amplifier 247 to amplifier 207 of integrator 63 (FIG. 10) and through resistor 256 and variable resistance 257 (to vary gain for calibration purposes) to the negative input of amplifier 68, the output of which is coupled to multiplexer 70 (FIG. 12). The output from voltage reference generator 60 is also coupled through resistor 260 and amplifier 261 to A/D converter 72 (FIG. 12).

Referring now to FIG. 12, the output from amplifier 67 (FIG. 11) is coupled through resistor 266 and sample-and-hold 267 (which also receives an input from gate 105 (FIG. 6)) to multiplexer 70. In like manner, the output from amplifier 68 (FIG. 11) is coupled through resistor 271 and sample-and-hold 272 (which also receives an input from gate 205 (FIG. 6)) to multiplexer 70. Although only two channels have been illustrated herein, it is to be realized that additional channels could be utilized as needed.

The output from multiplexer 70 is coupled from pin 3 through resistor 277 to pin 14 of A/D converter 72. A/D converter 72 provides a plurality of outputs to conventional digital processor 30.

A list of components which have been utilized in a working embodiment of this invention is set forth hereinafter. It is to be realized, however, that the invention is not meant to be limited to the components as listed. The component list is as follows:

Resistors: 77-1M; 89-3K; 92-10K; 95-10K; 103-20K; 104-10K; 108-10K; 110-82K; 112-9.1K; 114-82K; 116-9.1K; 121-100; 122-27; 123-200; 128-1K; 130-510K; 141-5.6K; 142-6.8K; 143-8.2K; 144-12K; 145-18K; 146-36K; 147-100K; 150-100K; 151-100K; 152-20K; 153-20K; 163-10K; 164-10K; 164-10K; 173-160K; 179-5.49K; 180-16.4K; 182-5.49K; 186-5.49K; 187-5.49K; 200-13.3K; 203-2.4M; 206-2.4M; 212-20K; 220-130K; 227-130K; 233-33K; 234-33K; 240-133K; 241-97.6K; 242-147K; 244-133K; 245-33K; 246-33K; 250-133K; 251-133K; 253-1K; 254-20K; 256-820; 257-0 to 500; 258-20K; 260-97.6K; 262-47K; 263-97.6K; 266-10K; 271-10K; 277-590K; 278-590K; 280-100; 282-147K; and 284-39K.

Capacitors: 124-22 $\mu$F; 129-4.7$\mu$; 131-10PF; 166 & 167-4.7 $\mu$F; 174 & 175-0.47 $\mu$F; 201-270PF; 205-0.47 $\mu$F; 208-0.47 $\mu$F; 219 & 226-4.7 $\mu$F. 223 and 230-0.01 $\mu$F; 236 & 237-0.47 $\mu$F; 243-4.7 $\mu$F; 248 & 249-0.47 $\mu$F; 268-0.1 $\mu$F; 269-0.047 $\mu$F; 273-0.1 $\mu$F; 274-0.047 $\mu$F; 279-68pF; 281-270pF; 283-0.1 $\mu$F; and 285-0.1 $\mu$F.

Transistors: 118 & 119-2N2219; 189 & 190-2N3904; and 215-2N3906.

Diodes: 1N914

NOR Gates: 4001B

Crystal: 76-1.832 MHz

Multiplexer: 70-4051

A/D Converter: 72-8702

Digital Processor: 6502

Analog Switches: 4051B

Integrated Circuits: 84-74LS90; 85-74LS107; 86-4007; 87-40408; 97-4555B; 99-4073; 100-4073; 136, 137 & 140-4051B; and 138-4024.

Amplifiers: 67 & 68-LM324; 111 & 115-LM324; 127-LF356; 161,178,181,183 & 184-TL084C; 199, 204 & 207-TL084C; 214-LM324; 224 & 231-TL084C; 235, 239 & 247-LM324; and 261-LM324.

Sample-and-hold: 267 and 272-LF398.

Switches: 168, 168, 170 & 171-4016; 176, 177 & 210-4053; and 221, 222, 228 & 229-4016.

Operational Transconductance Amplifier: LM13600.

The flow diagram for processor 72 is shown in FIG. 13, with definitions for the flow diagram being as follows:

A: Sampled Analog Channel A (R where channel A is in Red Region)
B: Sampled Analog Channel B (IR where channel B is in Infrared Region)
$\Delta$A: $A_{new} - A_{old}$
$\Delta$B: $B_{new} - B_{old}$
P: $P = |\Delta A + 4 \times 66 B|$ (proportional to blood thickness change)
OS: Oxygen saturation computed point by point
a,b,c&d: Constants used in OS calculation
W: $W = 1 + |OS - OT|$
F: $F = P/W$
WS: $WS = F \times OS$
SF: Sum of loop max F's
SW: Sum of loop max W's
LW: Running sum of 9 SW's
LF: Running sum of 9 SF's
OT: Final oxygen saturation calculation
LOOPMAX: A constant equal to 10 or 20 depending on status of front panel switches
LOOPCOUNT: A counter
THRESHOLD: A constant used to compare with LF to determine if perfusion is too low
OFF EAR FLAG: Flag which is high if an off ear condition is sensed The fundamental equation is:

$$\frac{\Delta I(\lambda)}{I(\lambda)} = \Delta L K(\lambda) \tag{1}$$

where
$\Delta L$ = The change in blood thickness
$K(\lambda)$ = The attenuation coefficient of the blood at wavelength $\lambda$
$\Delta I(\lambda)$ = The change in electromagnetic intensity at the measurement site at wavelength $\lambda$
$I(\lambda)$ = The average electromagnetic intensity at the measurement site at wavelength $\lambda$.

It follows immediately from equation (1) that if $K(\lambda)$ is known, $\Delta L$ may be calculated by measuring $\Delta I(\lambda)$ and $I(\lambda)$.

For blood in living tissue, the attenuation coefficient, $K(\lambda)$, is generally the result of a linear combination of the attenuation coefficients of two or more attenuating substances, such as hemoglobin (Hb), oxyhemoglobin (HbO$_2$) and carboxyhemoglobin (HbCO):

$$K(\lambda) = \frac{\Delta L^{A1}}{\Delta L} K(\lambda)^{A1} + \frac{\Delta L^{A2}}{\Delta L} K(\lambda)^{A2} \ldots + \frac{\Delta L^{Am}}{\Delta L} K(\lambda)^{Am} \tag{2}$$

where the superscripts $A_1$ through $A_m$ indicate that the associated quantities relate to the different attenuating substances which are designated $A_1$ through $A_m$.

It is to be understood that the total volume change is, $$\Delta L = \Delta L^{A1} + \Delta L^{A2} \ldots + \Delta L^{Am} \tag{3}$$

Combining equations (1) and (2) results in a general expression:

$$\frac{\Delta I(\lambda)}{I(\lambda)} = K(\lambda)^{A1}\Delta L^{A1} + K(\lambda)^{A2}\Delta L^{A2} \ldots + K(\lambda)^{Am}\Delta L^{Am} \tag{4}$$

By making measurements of $$\frac{\Delta I(\lambda)}{I(\lambda)}$$

at "m" different wavelengths ($\lambda_1, \lambda_2, \ldots \lambda_m$), a set of linear equations results which may be solved simultaneously for $\Delta L^{A1}$ through $\Delta L^{Am}$.

The general form of this solution is:

$$\Delta L^{An} = N_1 R(\lambda_1) + N_2 R(\lambda_2) \ldots + N_m R(\lambda_m) \tag{5}$$

where $A_n$ designates the nth attenuator of "m" attenuators $$R(\lambda) = \frac{\Delta I(\lambda)}{I(\lambda)}$$

$N_1$ through $N_m$ are constants related to the nth attenuator and the specific wavelengths $\lambda_1$ through $\lambda_m$.

The fractional or percentage concentration of any of the attenuators is, from equation (5):

$$\%A_n = 100\left[\frac{\Delta L^{A_n}}{\Delta L}\right] \quad (6)$$

where $\Delta L$ is defined by equation (3).

An example of this is the determination of Oxygen Saturation (O.S.) which is the percentage of oxyhemoglobin relative to total hemoglobin:

$$O.S. = 100 \quad (7)$$

$$\left[\frac{N_1^{HbO2} R(\lambda_1) + N_2^{HbO2}(R\lambda_2)}{(N_1^{HbO2} + N_1^{Hb}) R(\lambda_1) + (N_2^{HbO2} + N_2^{Hb}) R(\lambda_2)}\right]$$

Equation (7) may be simplified and rewritten:

$$O.S. = \frac{X_1 R(\lambda_1) + X_2 R(\lambda_2)}{X_3 R(\lambda_1) + X_4 R(\lambda_2)} \quad (8)$$

where the constants $X_1$ through $X_4$ may be derived if the appropriate physical constants are known, or they may be calculated by curve fitting techniques using empirical measurements of the ratio $$\frac{R(\lambda_1)}{R(\lambda_2)} \quad (9)$$

versus simultaneous standard blood gas determinations.

Thus the simplified, general equation is of the form:

$$\%A_n = \frac{X_1 R(\lambda_1) + X_2 R(\lambda_2) \ldots + X_m R(\lambda_m)}{X_{m+1} R(\lambda_1) + X_{m+2} R(\lambda_2) \ldots + X_{2m} R(\lambda_m)} \quad (10)$$

In the present invention, the quantities $\Delta I(\lambda)$ and $I(\lambda)$ are converted by a detector to electronic signals, $AC(\lambda)$ and $DC(\lambda)$, respectively, which are representative of the magnitudes of the electromagnetic quantities. Therefore, in equation (10), the terms $R(\lambda)$ may be represented by:

$$R(\lambda) = \frac{AC(\lambda)}{DC(\lambda)} \quad (11)$$

wherein the $AC(\lambda)$ term may be a representation of the peak-to-peak amplitude or any portion thereof, the peak-to-peak amplitude (or any portion thereof) of the first or higher derivatives, or the differential of the $AC(\lambda)$ term or any of its first or higher derivatives. The $AC(\lambda)$ term may also be a representation as described above of any of the spectral components or any transformation thereof as produced by analog or digital processing.

In equation (11), $R(\lambda)$ may be a representation of a typical average or "best estimate" value of the ratio as produced by the invention herein described.

The general algorithm for processor 30 is set forth in FIG. 14, the use of which causes operation of the processor to determine oxygen saturation of blood through measurement of blood thickness changes with respect to the specific device set forth hereinabove. The device could, however, be adapted for use in measuring many other constituents of blood utilizing the general algorithm as set forth in FIG. 14. To utilize the algorithm for determining other constituents of blood, it is necessary that the number of wavelengths be equal to or greater than the number of unknown constituents. For example, the device and method can be used to determine constituents such as carboxyhemoglobin, carbon dioxide in blood and/or blood glucose. The essential is that the constituent be determinable through measurement of changes in blood thickness relative to total thickness, and therefore the device and method can also be utilized to measure hematocrit (i.e., percent of packed blood cells relative to total blood volume) and/or total blood volume change in a tissue segment (plethysmography) and/or total blood flow through a tissue segment per unit time.

From the foregoing it should be realized that this invention provides a blood constituent measuring device and method one use of which is to provide an improved oximetry device and method.

What is claimed is:

1. A blood constituent measuring device, comprising:
   electromagnetic energy emitting means for emitting electromagnetic energy at a plurality of predetermined wavelengths through a blood-containing sample at a test area;
   sensing means for receiving electromagnetic energy from said sample at said plurality of wavelengths;
   signal producing means connected with said sensing means to produce output signals responsive to electromagnetic energy received by said sensing means at said plurality of wavelengths;
   normalizing means for receiving said output signals from said signal producing means and scaling the same so that the DC components are normalized; and
   processing means for receiving said output signals from said normalizing means and producing an output indicative of changes in the thickness of preselected constituents of blood relative to the total change in blood thickness.

2. The device of claim 1 wherein said processing means includes means for separating said output signals into separate channels each of which is related to a different one of said plurality of wavelengths of electromagnetic energy emitted by said electromagnetic energy emitting means.

3. The device of claim 2 wherein said device includes timing means connected with said electromagnetic energy emitting means, normalizing means and processing means for controlling separation of said input signals into said separate channels at said processing means and for causing scaling of said output signals.

4. The device of claim 3 wherein said timing means causes said electromagnetic energy emitting means to be sequentially energized for predetermined time periods to cause a train of pulses to be produced by said signal producing means as said output signals coupled to said normalizing means.

5. The device of claim 1 wherein said output signals from said signal producing means include AC and DC components, and wherein said normalizing means includes means for providing a signal proportional to the quotient of the AC component and DC component.

6. A blood constituent measuring device, comprising:
   timing means;

first and second light emitting diodes connected with said timing means to cause light to be sequentially emitted at different wavelengths toward a test area;

photodiode means for receiving light from said light emitting diodes after said light has passed through said test area, said test area being adapted to receive a tissue sample having blood moving therein;

current to voltage converting means connected with said photodiode means to produce a train of AC modulated pulses when light is received at said photodiode means from said light emitting diodes;

normalization means connected with said current to voltage converting means to receive said train of pulses therefrom and normalize said pulses by scaling said pulse developed by light from each of said light emitting diodes so that the average component of each of said pulses developed by light from one of said light emitting diodes is equal to the average component from each of said pulses developed by light from the other of said light emitting diodes;

first and second decoding means connected with said normalizing means and said timing means to receive said normalized train of pulses and produce separate outputs in first and second separated channels with the signal in said first channel being developed from light from said first light emitting diode and the signal in said second channel being developed from light from said second light emitting diode;

first and second low pass filter means connected with said first and second decoding means in said first and second channels so that said first low pass filter means receives said signal from said first decoding means and said second low pass filter means receives said signal from said second decoding means;

voltage reference generator means connected with said first and second low pass filter means to supply a DC voltage to said first and second low pass filter means;

first and second integrator means connected with said first and second low pass filter means to receive said pulses therefrom;

first multiplexing means connected with said first and second integrator means and said normalization means;

second multiplexing means connected with said first and second low pass filter means to receive said output therefrom and provide a multiplexed output;

analog to digital converter means connected with said second multiplexing means; and digital processing means connected with said analog to digital converter means and responsive to inputs therefrom providing an output indicative of changes in the thickness of preselected constituents of blood relative to the total change of blood thickness in the tissue sample at said test area.

7. A blood constituent measuring device, comprising:
light emitting means for emitting light through a blood-containing sample;
light sensing means for receiving light from said sample at said plurality of wavelengths;
signal producing means connected with said light sensing means to produce output signals responsive to light received by said light emitting means at said plurality of wavelengths; and processing means including a processor for receiving said output signals from said signal producing means and producing an output indicative of oxygen saturation of blood in said tested sample, said processor determining said oxygen saturation thereof through measurement of blood thickness changes of said sample at said test area and using the relationship % concentration = 100

$$\left[ \frac{X_1 R(\lambda_1) + X_2 R(\lambda_2) \ldots + X_m R(\lambda_m)}{X_{m+1} R(\lambda_1) + X_{m+2} R(\lambda_2) \ldots + X_{2m} R(\lambda_m)} \right]$$

where the constants $X_1 \ldots X_{2m}$ are chosen for the particular constituent for determining changes in the thickness of preselected constituents of blood relative to the total change in the thickness of blood in the sample in the test area and $R(\lambda_1) \ldots R(\lambda_m)$ is the ratio of the AC to DC components of received light at the respective frequency.

8. The device of claim 7 wherein said processing means includes means to separate said output signals received from said signal producing means into different channels, and wherein said device includes timing means connected with said light emitting means and said processing means whereby said output signals received by said signal processings means are separated into channels according to wavelengths of emitted light causing said output signal to be produced at said signal producing means.

9. The device of claim 7 wherein said device includes normalizing means connected with said signal producing means and said processing means to scale said output signals received from said signal producing means to normalize said output signals so that the DC components are equal prior to coupling of said output signals to said processing means.

10. A blood thickness change measuring device, comprising:
electromagnetic energy emitting means for emitting electromagnetic energy at a blood-containing sample to be tested;
sensing means for receiving electromagnetic energy from said sample;
signal producing means connected with said sensing means to produce output signals having an AC and a DC component with said output signals being produced responsive to electromagnetic energy received by said sensing means;
normalizing means for receiving said output signals from said signal producing means and scaling said signals so that the DC components of each are equal; and
processing means for receiving said output signals from said normalizing means and responsive thereto producing an output indicative of blood thickness changes in said tested sample.

11. The device of claim 10 wherein said electromagnetic energy emitting means emits electromagnetic energy at a plurality of predetermined wavelengths at said sample, wherein said sensing means receives electromagnetic energy at said plurality of wavelengths and produces output signals indicative thereof, and wherein said processing means includes signal separation means for dividing said output signals received from said sensing means into a plurality of channels equal in number to said plurality of wavelengths of electromagnetic energy emitted by said electromagnetic energy emitting means and producing an output signal in each of said channels indicative of electromagnetic energy emitted from a different one of each of said plurality of wavelengths of electromagnetic energy emitted by said electromagnetic energy emitting means.

12. The device of claim 11 wherein said device includes timing means connected with said electromagnetic energy emitting means and said processing means so that said timing means causes said electromagnetic energy emitting means to be sequentially energized for predetermined time periods to cause a train of pulses to be produced by said signal producing means as the output signal therefrom.

13. A method for indicating the relative amounts of predetermined blood constituents in a blood-containing sample, said method comprising:
   directing electromagnetic energy at a plurality of wavelengths through a sample to be tested;
   collecting electromagnetic energy from said sample at said plurality of wavelengths and forming electronic signals indicative thereof;
   normalizing said electronic signals by scaling the DC components with respect to each other; and
   processing said signals after said signals have been normalized to indicate from the measured change in thickness of said predetermined blood constituents relative to the total change in blood thickness, the amount of said constituents in the blood-containing sample tested.

14. The method of claim 13 wherein normalizing of said electronic signals includes dividing the AC component of each signal by the DC component and multiplying by a predetermined constant.

15. A method for determining the relative amounts of predetermined blood constituents in a blood-containing sample, the method comprising:
   sequentially directing light at at least two different wavelengths through a sample to be tested;
   collecting light from said sample and developing therefrom a pulse train indicative of received light at both of said wavelengths;
   normalizing the pulses from said pulse train by scaling said pulses so that the average components of said pulses are equal;
   separating the pulses of said pulse train into first and second channels with the pulses in said first channel being indicative of light emitted at one wavelength and the pulses in the second channel being indicative of light emitted at the other wavelength of said two different wavelengths;
   then multiplexing said signals in each channel;
   converting said multiplexed signals to digital signals; and
   digitally processing said signals to provide an indication of the amount of each predetermined constituent in the blood of said sample.

16. The method of claim 15 wherein digital processing is carried out using the relationship % concentration = 100

$$\left[ \frac{X_1 R(\lambda_1) + X_2 R(\lambda_2) \ldots + X_m R(\lambda_m)}{X_{m+1} R(\lambda_1) + X_{m+2} R(\lambda_2) \ldots + X_{2m} R(\lambda_m)} \right]$$

where $X_1 \ldots x_{2m}$ are constants chosen for the particular constituent and $R(\lambda_1) \ldots R(\lambda_m)$ are the ratios of the AC and DC components of the light at the respective wavelengths.

17. A method for determining the relative amounts of predetermined blood constituents in a blood-containing sample at a test area, said method comprising:
   directing light at at least two wavelengths at a blood-containing sample at a test area;
   collecting light from the sample and developing electronic signals in digital form indicative of light collected at the two wavelengths of light directed to the sample; and
   processing the electronic signals in a digital processor to provide an output indicative of the relative amounts of said predetermined blood constituents through measurement utilizing the relationship % concentration = 100

$$\left[ \frac{X_1 R(\lambda_1) + X_2 R(\lambda_2) \ldots + X_m R(\lambda_m)}{X_{m+1} R(\lambda_1) + X_{m+2} R(\lambda_2) \ldots + X_{2m} R(\lambda_m)} \right]$$

where $X_1 \ldots X_2$ are chosen for the particular constituent.

18. A method for determining the relative amounts of predetermined blood constituents in a blood-contain sample at a test area, said method comprising:
   positioning a blood-containing sample at a test area;
   directing light at the sample at the test area and collecting therefrom the light at at least two different wavelengths;
   developing electronic signals with respect to light collected at the two different wavelengths;
   normalizing the electronic signals developed from each of the two different wavelengths so that the DC components are equal;
   simultaneously sampling the normalized electronic signals developed from each of the two different wavelengths;
   calculating from the samples the ΔAC for each signal where ΔAC equals the algebraic difference between two consecutive samples of one signal;
   calculating an estimate of the relative amount of each constituent by the equation, percent saturation equals 100

$$\frac{X_1 R(\lambda_1) + X_2 R(\lambda_2) \ldots + X_m R(\lambda_m)}{X_{m+1} R(\lambda_1) + X_{m+2} R(\lambda_2) \ldots + X_{2m} R(\lambda_m)}$$

where $X_1 \ldots X_{2m}$ are constants chosen for the particular constituent and wavelength and $R(\lambda_1) \ldots R(\lambda_m)$ are the ratios of the AC and DC components of the respective wavelength;
   calculating weighting factors which are functions of the magnitude of the ΔAC's and also the difference between the estimate and the final calculation of the relative amount of each constituent;
   multiplying the appropriate weighting factors by the estimates of each of said constituents;
   accumulating a number of weighting factors and an equal number of weighting factors multipled by the estimates of each of said constituents;
   performing a final calculation of relative amounts of each constituent by dividing accumulated products by accumulated weighting factors; and 19. A method for determining oxygen saturation of blood, said method comprising:
directing electromagnetic energy at a plurality of wavelengths toward a sample to be tested for oxygen saturation of blood;
collecting electromagnetic energy from said sample at said plurality of wavelengths and forming electronic signals indicative thereof;
normalizing said electronic signals by scaling the DC components of each to a predetermined reference level; and
processing said signals after said signals have been normalized to indicate the percentage of oxygen saturation of blood in said sample.

20. The method of claim 19 wherein signals formed from collected electromagnetic energy are processed in a plurality of channels equal in number to the plurality of wavelengths of emitted electromagnetic energy with an output from each of said channels being utilized to determine the percentage of oxygen saturation of blood in the sample.

21. The method of claim 20 wherein said processing of said signals includes determining changes in blood thickness containing oxyhemoglobin relative to total change in blood thickness to enable said indication of the percentage of oxygen saturation of blood.

22. The method of claim 20 wherein said electromagnetic energy is emitted sequentially at said different wavelengths so said electromagnetic energy is collected to form a train of pulses as said electronic signals.

23. The method of claim 19 wherein normalizing of said electronic signals includes dividing the AC component of each signal by the DC component and multiplying by a predetermined constant.

24. A method for determining oxygen saturation of blood, comprising:
sequentially directing light at at least two different wavelengths at a sample to be tested for oxygen saturation of blood;
collecting light from said sample and developing therefrom a pulse train indicative of received light at both of said wavelengths;
normalizing the pulses of said pulse train by scaling said pulses so that the average components of said pulses are equal;
separating the pulses of said pulse train into first and second channels with the pulses in said first channel being indicative of light emitted at one wavelength and the pulses in the second channel being indicative of light emitted at the other wavelength of said two different wavelengths;
then multiplexing said signals in each channel;
converting said multiplexed signals to digital signals; and
digitally processing said signals to provide an indication of oxygen saturation in the blood of said sample.

25. A method for determining blood thickness changes, said method comprising:
directing electromagnetic energy toward a blood-containing sample at a test area;
collecting electromagnetic energy from the sample at the test area and providing from the collected electromagnetic energy electronic signals having a DC and an AC component;
normalizing the electronic signals by scaling the signals so that the DC components are equal; and
processing the normalized electronic signals to provide an output indicative of blood thickness changes in the sample tested.

26. The method of claim 25 wherein electromagnetic energy is emitted at a sample at a plurality of predetermined wavelengths, and wherein electromagnetic energy is collected with respect to the plurality of wavelengths of emitted electromagnetic energy and electronic signals developed with respect to each of said wavelengths with each of said electronic signals thus developed being normalized by scaling said signals.

27. The method of claim 26 wherein said electromagnetic energy is emitted in bursts and said electronic signals are pulses each of which is normalized by scaling.

28. The method of claim 25 wherein normalizing of said electronic signals includes dividing the AC component of each signal by the DC component and multiplying by a predetermined constant.

29. An apparatus for measuring at least one constituent of blood in tissue comprising means for selectively passing light of a plurality N of wavelengths through said tissue, wherein N is at least equal to the number of constituents to be measured, means for sensing said light and producing a plurality of signals corresponding to the attenuation of said light at the respective wavelengths, means for adjusting the average levels of said signals to be equal to each other or to a determined quantity, and data processing means responsive to said adjusted signals for determining the quantity of said constituents.

30. The apparatus of claim 29 wherein said means for passing light through said tissue comprises a plurality of separate light emitters and means for sequentially energizing the said emitters, and said means for sensing said light and producing signals comprises photosensitive means, whereby the output of said photosensitive means comprises alternate sequences of pulses corresponding to the respective separate light emitters.

31. The apparatus of claim 30 wherein one of said emitters emits light in the infrared region and another of said emitters emits light in the red region.

32. The apparatus of claim 30 wherein said means for adjusting comprises an operational transconductance amplifier means having first and second inputs, low pass filter means applying signals from said photosensing means to one of said inputs, and means directed upon the signals from said photosensitive means to the other input of said transconductance amplifier means, and intergrator means connected to control the transconductance of said amplifier means by the time integral of the signal output of the transconductance amplifier means.

33. The apparatus of claim 29 wherein said means responsive to said adjusted signals comprises data processing means for solving the expression;

$$\frac{\Delta I(\lambda)}{I(\lambda)} = K(\lambda)^{A1}\Delta L^{A1} + K(\lambda)^{A2}\Delta L^{A2} \ldots + K(\lambda)^{Am}\Delta L^{Am}$$

for $\Delta L^{A1}$ through $\Delta L^{Am}$, wherein $K(\lambda)^{A1} \ldots K(\lambda)^{Am}$ are the attenuation coefficients of blood at the respective wavelengths with the $^{A1} \ldots ^{Am}$ indicating the associated quantities relating to different attenuating substances, and $\Delta I(\lambda)$ and $I(\lambda)$ are the varying and constant components respectively of the input signals to the data processing means, at the respective wavelengths.

34. The method of measuring one or more determined constituents of blood, comprising sensing the attenuation of light passing through tissue containing the blood at a plurality of different wavelengths at least equal in number to the number of said constituents to be determined, to produce a quantity at each wavelength corresponding to the portion of the variation of attenuation divided by the average attenuation, calculating the quantity of each said constituent indicated at each wavelength, and determining the quantity of each said constituents by summing the quantities determined thereof at each wavelength.

35. The method according to claim 34 wherein said step of calculating the quantity of each said constituent comprises solving the relationship;

$$\frac{\Delta I(\lambda)}{I(\lambda)} = K(\lambda)^{A1}\Delta L^{A1} + K(\lambda)^{A2}\Delta L^{A2} \ldots + K(\lambda)^{Am}\Delta L^{Am}$$

for $\Delta L^{A1}$ through $\Delta L^{Am}$, which represent the quantities of constituents $1 \ldots m$, wherein $K(\lambda)^{A1} \ldots K(\lambda)^{Am}$ are the attenuation coefficients of blood at the respective wavelength $\lambda$ which relates to the different attenuating substances designated $A_1 - A_m$, and the quantity $$\frac{\Delta I(\lambda)}{I(\lambda)}$$

corresponding to said quotient at each respective wavelength.

36. The method of claim 35 further comprising solving the relationship;

$$\% A_n = 100 \left[\frac{\Delta L^{An}}{\Delta L}\right]$$

for determining the percentage concentration $\% A_m$ of each constituent, and $\Delta L$ is the sum of the quantities of the various constituents.

* * * * *

UNITED STATES PATENT AND TRADEMARK OFFICE
CERTIFICATE OF CORRECTION

PATENT NO. : 4,407,290

DATED : October 4, 1983

INVENTOR(S) : SCOTT A. WILBUR

It is certified that error appears in the above—identified patent and that said Letters Patent is hereby corrected as shown below:

Col. 1, lines 37 and 47, change "3,804,539" to --3,804,535--;
        line 59, change "4,167,339" to --4,167,331--.
Col. 4, line 6, delete "a";
        line 7, change "application" to --No. 4,394,572--;
        line 56, change "exagerated" to --exaggerated--.
Col. 5, line 63, change "capacators" to --capacitors--.
Col. 6, line 15, change "KHz" to --kHz--.
Col. 7, line 28, change "side" to --sides--.
Col. 11, line 15, change "(R$\lambda_2$)" to --R($\lambda_2$)--.
Col. 12, line 7, insert --aspect-- before "is".
Col. 14, line 29, change "processings" to --processing--.
Col. 16, line 26, change "blood-contain" to --blood-containing--.
Col. 18, line 51, change "intergrator" to --integrator--.

Signed and Sealed this

Twenty-second Day of January 1985

[SEAL]

Attest:

DONALD J. QUIGG

Attesting Officer     Acting Commissioner of Patents and Trademarks

REEXAMINATION CERTIFICATE (584th)

United States Patent [19]

Wilber

[11] B1 4,407,290

[45] Certificate Issued  Oct. 14, 1986

[54] BLOOD CONSTITUENT MEASURING DEVICE AND METHOD

[75] Inventor: Scott A. Wilber, Boulder, Colo.

[73] Assignee: Biox Technology, Inc., Boulder, Colo.

Reexamination Request:
No. 90/000,794, Jun. 10, 1985

Reexamination Certificate for:
Patent No.: 4,407,290
Issued: Oct. 4, 1983
Appl. No.: 250,956
Filed: Apr. 1, 1981

Certificate of Correction issued Jan. 22, 1985.

[51] Int. Cl.$^4$ .............. G01N 33/16; A61B 5/00
[52] U.S. Cl. .................. 128/633; 128/653; 128/665; 356/41; 364/416
[58] Field of Search ............. 128/632, 633, 634, 664, 128/665, 666, 667; 356/39, 40, 41; 364/416

[56] References Cited

U.S. PATENT DOCUMENTS

| | | | |
|---|---|---|---|
| 2,706,927 | 4/1955 | Wood | 128/633 |
| 3,522,739 | 8/1970 | Coor et al. | 356/97 |
| 3,998,550 | 12/1976 | Konishi et al. | 356/39 |
| 4,063,551 | 12/1977 | Sweeney | 128/666 |
| 4,086,915 | 5/1978 | Kofsky et al. | 356/41 X |
| 4,167,331 | 9/1979 | Nielsen | 128/633 X |
| 4,201,222 | 5/1980 | Haase | 128/634 |
| 4,266,554 | 5/1981 | Hagamuri | 128/633 |

FOREIGN PATENT DOCUMENTS

128387  10/1975  Japan .

OTHER PUBLICATIONS

Nakajima et al, "Performance of New Pulsed Type Ear Piece Oximeter".
Wood et al, "Photoelectric Determination of Arterial Oxygen Saturation in Man".
Zilstra et al, "Medical Reflection Photometry" 1962.
Yoshiya et al, "Spectrophotometric Monitoring . . . ", Med. & Biol. Eng. Comput., Jan. 1980, pp. 27-32.

*Primary Examiner*—Lee S. Cohen

[57] ABSTRACT

A non-invasive blood constituent measuring device and method are disclosed for measuring changes in blood thickness of predetermined blood constituents relative to total change in blood thickness at a test area to thereby determine the concentration of such constituents in the blood in a living body, which measured constituents may be, for example, hemoglobin and oxyhemoglobin to enable determination of oxygen saturation of blood. The device includes a plurality of light emitting diodes operationally controlled by timing circuitry for sequentially emitting light at different predetermined wavelengths toward a blood containing tissue sample, such as an ear lobe. A linear sensor receives emitted light passing through the sample and a train of AC modulated pulses indicative thereof is formed and then the signal representative of the light received from each emitter is scaled so that the DC components of each are normalized to a predetermined reference level with the pulse train being divided into channels at a decoder where remaining DC offset is removed and the DC component in each channel is then removed at a low pass filter, after which the AC signals in each channel are multiplexed and converted to a digital signal indicative of changes in the thickness of blood constituents for processing in a digital processor to determine therefrom the saturation of the measured blood constituents. A test unit is also included for testing operation of the device by introducing known AC modulated test signals into the circuitry.

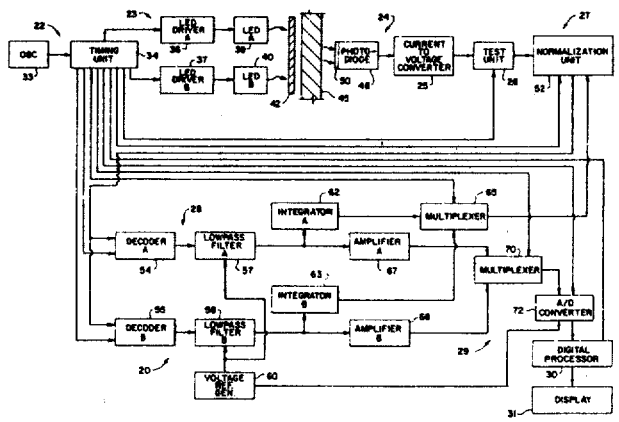

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1-6, 10-16 and 18-33 is confirmed.

Claims 7-9, 17 and 34-36 are cancelled.

* * * * *